United States Patent [19]

Deschamps et al.

[11] Patent Number: 4,810,692

[45] Date of Patent: Mar. 7, 1989

[54] IMMUNOSUPPRESSANT SUBSTANCES, PROCESS FOR THEIR PREPARATION AND PHARMACEUTICAL COMPOSITIONS CONTAINING THEM

[75] Inventors: Maurice Deschamps, Saint-Maur; Francois Floc'h, Perigny; Gerard Jung, Leuville Sur Orge; Rodolphe Margraff, Viry Chatillon, all of France

[73] Assignee: Rhone-Poulenc Sante, Courbevoie, France

[21] Appl. No.: 52,388

[22] Filed: May 21, 1987

[30] Foreign Application Priority Data

May 22, 1986 [FR] France .................. 86 07269

[51] Int. Cl.[4] .................. A61K 37/02; C07K 7/54
[52] U.S. Cl. .................. 514/11; 530/317
[58] Field of Search .................. 530/317, 321, 323; 514/11

*Primary Examiner*—Delbert R. Phillips
*Assistant Examiner*—Christina Chan
*Attorney, Agent, or Firm*—Stevens, Davis, Miller & Mosher

[57] ABSTRACT

The invention provides two novel immunosuppressant cyclodepsipeptides of formula:

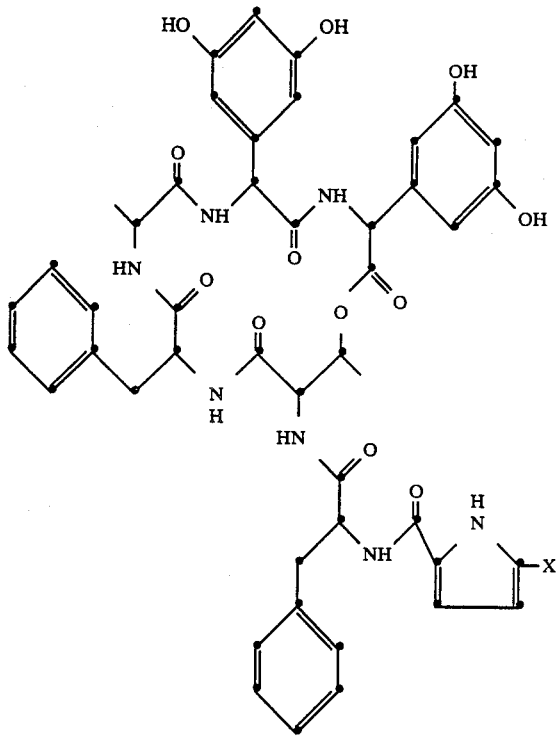

in which X is chlorine or hydrogen. These compounds may be made by culturing *Streptomyces sp.* S-16328 (CBS 162.86). The compound in which X is chlorine may be hydrogenolysed to give the compound in which X is hydrogen.

4 Claims, 4 Drawing Sheets

IMMUNOSUPPRESSANT SUBSTANCES, PROCESS FOR THEIR PREPARATION AND PHARMACEUTICAL COMPOSITIONS CONTAINING THEM

The present invention relates to immunosuppressant substances, their preparation and pharmaceutical compositions which contain them.

The invention provides two novel immunosuppressant substances, herein called 55185 RP and 59451 RP, which can be obtained from culture media of a new microorganism, described more completely below, belonging to the genus Streptomyces and called herein Streptomyces sp. S-16328 (CBS 162.86).

55185 RP and 59451 RP are cyclodepsipeptides which have the general formula:

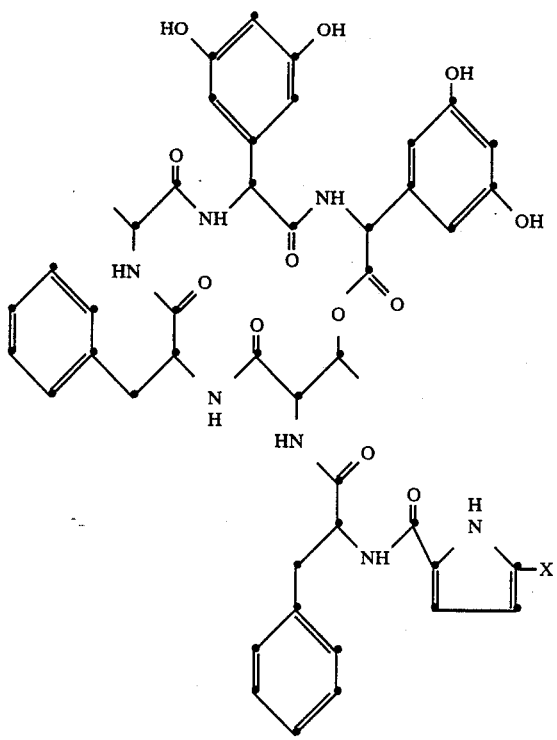

in which X is a chlorine atom (in 55185 RP) or hydrogen atom (in 59451 RP).

55185 RP is characterized by the following physicochemical properties:

appearance: white to pale yellow amorphous powder solubility: soluble in methanol, ethanol, ethyl acetate, acetone, acetonitrile, dimethylformamide, and dimethyl sulphoxide, and insoluble in water (0.1 to 0.3% regardless of the pH), ethyl ether and hexane;

percentage composition: 55185 RP corresponds to the empirical formula $C_{46}H_{46}ClN_7O_{12}$. The percentage composition is:

|  | calculated | found |
|---|---|---|
| C % | 58.47 | 58.29 |
| H % | 4.58 | 5.30 |
| Cl % | 3.84 | 3.84 |
| N % | 10.61 | 10.13 |
| O % | 22.50 | 22.57 | melting point: above 300° C.

optical rotation: $[\alpha]_D^{20} = +20.5° \pm 1.4°$ (c=0.5; methanol).

The structure of 55185 RP was determined from its ultraviolet, infrared and mass spectra and proton and $^{13}C$ nuclear magnetic resonance spectra.

Ultraviolet spectrum: (determination using a methanolic solution containing 267.5 μg/ml, on a thickness of 1 mm):

$\lambda max = 274$ nm ($E_{1\ cm}^{1\%} = 219$, $\epsilon = 20240$)

A shoulder is observed at 230 nm.

The ultraviolet spectrum is not modified by adding hydrochloric acid. After adding sodium hydroxide, a bathochromic shift from 230 to 247 nm and from 274 to 295 nm is observed.

Figure 1:
FIGS. 1 and 2 of the accompanying drawings show respectively the ultra-violet and infra-red spectra of 55185 RP.

The ultraviolet spectrum of 55185 RP is shown in accompanying FIG. 1.

Infrared spectrum: (determination using tablets of a mixture with KBr)

Figure 2:
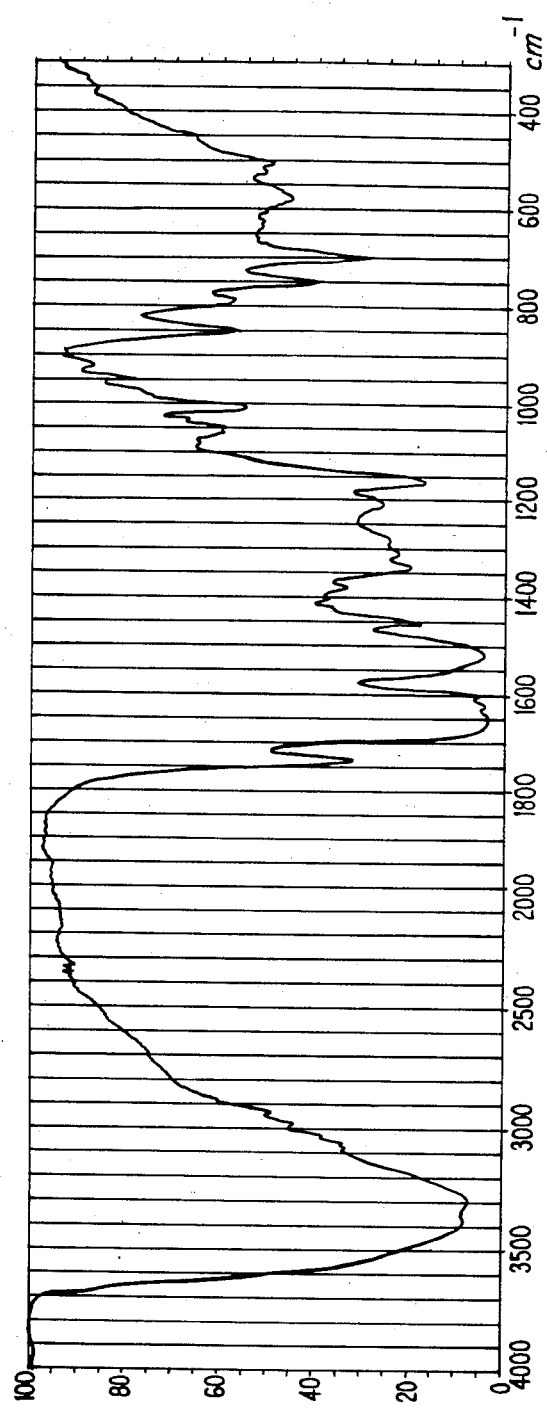

The infrared spectrum is shown in FIG. 2, in which the wave numbers in $cm^{-1}$ are plotted as abscissae and the optical densities as ordinates.

Table I shows the main infrared absorption bands of the product expressed in wave numbers ($cm^{-1}$).

TABLE I

| 3380 | vS | (including H2O) | 1520 | vS |  | 980 | sh |
|---|---|---|---|---|---|---|---|
| 3300 | vS |  | 1500 | sh |  | 950 | w |
| 3090 | w |  | 1455 | m |  | 925 | vw |
| 3060 | w |  | 1440 | sh |  | 900 | vw |
| 3030 | sh |  | 1425 | sh |  | 850 | m |
| 2980 | w |  | 1405 | w |  | 795 | sh |
| 2940 | w |  | 1380 | w |  | 785 | m |
| 2880 | sh |  | 1340 | m |  | 750 | m |
| 2700 | sh |  | 1310 | m |  | 700 | m |
| 2500 | sh |  | 1285 | w |  | 690 | sh |
| 2340 |  | $CO_2$ | 1215 | m |  | 635 | vw |
| 2160 | vw |  | 1205 | sh |  | 625 | vw |
| 1950 | sh |  | 1160 | S |  | 605 | sh |
| 1880 | vw |  | 1120 | sh |  | 580 | m |
| 1740 | S |  | 1080 | vw |  | 525 | w |
| 1680 | sh |  | 1060 | sh |  | 510 | w |
| 1655 | vS |  | 1050 | w |  | 495 | sh |
| 1625 | m |  | 1030 | vw |  | 455 | sh |
| 1605 | m |  | 1010 | sh |  | 400 | sh |
| 1555 | sh |  | 1000 | m |  | 355 | vw | vS = very strong
S = strong
m = moderate
w = weak
vw = very weak
sh = shoulder

Mass spectrum:

In FAB ionization (fast atom bombardment with an 8 keV base of xenon atoms) with a glycerol/thioglycerol mixture as matrix and in a mass range between 400 and 1000 AMU, the base peak is the pseudomolecular ion $MH^+ = 924$ showing an isotope complex characteristic of the presence of a chlorine atom.

The ions observed at masses m/z=650, m/z=567 and m/z=506 correspond to the fragments below:

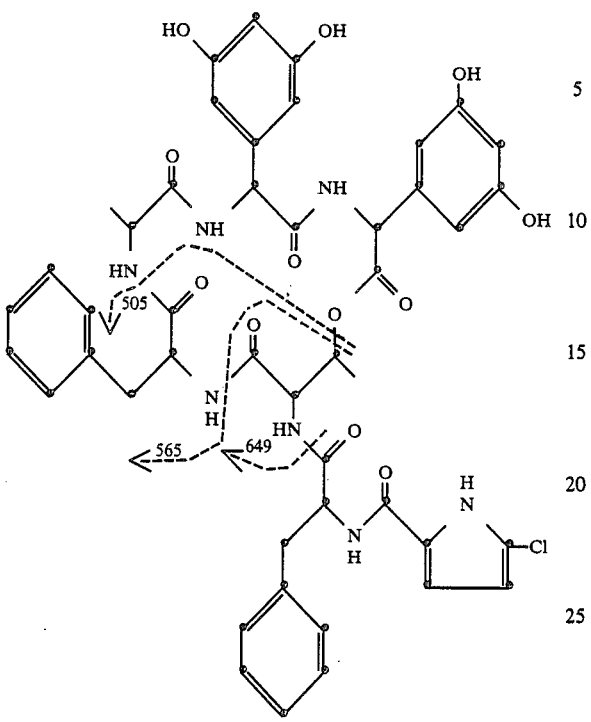

In desorption/chemical ionization (DCI) with $NH_3$ as the reactant gas, the final peak is observed at m/z=880 ($MH^+ - CO_2$). The fragments of mass 275 and 753 correspond to the following structures:

In electron impact (EI) (electron bombardment at 70 eV), the final peak is observed at mass m/z=521.

The fragments of mass m/z=91 and m/z=120 are characteristic of the presence of phenylalanine (F).

Proton and $^{13}C$ nuclear magnetic resonance spectra:

The spectra were recorded in DMSO-$d_6$, working at 400.13 MHz for protons and at 100.6 MHz for carbon at 40° C.

The assignments are given in ppm relative to the central line of DMSO (2.5 ppm for protons: 39.5 ppm for carbon).

The analysis of the proton nuclear magnetic resonance spectrum is given in Table II.

TABLE II

|  | Hα | Hβ | Hγ | NH | Aromatic | OH |
|---|---|---|---|---|---|---|
| T | 4.45 (a) | 4.98 (a) | 1.15 (d) J = 6 Hz | 8.6 (d) J = 9 Hz | — | — |
| A | 4.00 (a) | 1.38 (a) J = 7 Hz | — | 8.16 (d) J = 5 Hz | — | — |
| $F_1$ | 4.80 (a) | 2.80 ⎱ (a) 3.10 ⎰ | — | 8.09 (d) J = 9 Hz | 7.05 ⎱ (a) 7.30 ⎰ | — |
| $F_2$ | 4.55 (a) | 2.90 ⎱ (a) 3.15 ⎰ | — | 8.55 (d) J = 9 Hz | 7.05 ⎱ (a) 7.30 ⎰ | — |
| $FG_1$ | 5.45 (d) J = 9 Hz | — | — | 7.80 (d) J = 9 Hz | 6.22 ⎱ (s) 6.28 ⎰ | 9.23 (bs) |
| $FG_2$ | 5.25 (d) J = 8 Hz | — | — | 8.27 (d) J = 8 Hz | 6.15 ⎱ (s) 6.18 ⎰ | 9.14 (bs) |
| ClP | — | — | — | 12.1 (s) | 6.05 & 6.90 2 d J = 3.5 Hz | — |

The coupling constant J is expressed in Hz

| d = doublet | s = singlet |
|---|---|
| bs = broad singlet | m = multiplet |
| T = threonine | A = alanine |
| F = phenylalanine | FG = phenylglycine |
| ClP = chloropyrrole | |

The results for the assignments of $^{13}C$ are as follows:

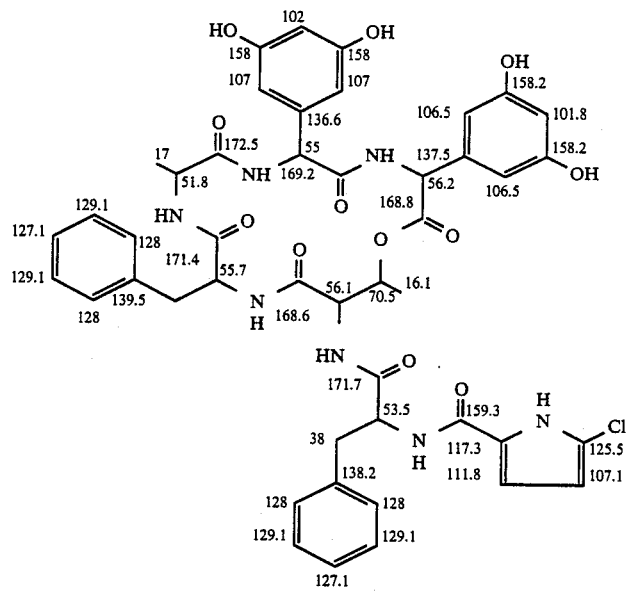

In ascending thin layer chromatography on silica gel, using a 1,2-dichloroethane/methane (80:20 by volume) solvent mixture, the Rf is in the region of 0.5. On a Merck silanized silica plate, using an acetonitrile/water containing 3% of NaCl (40:60 by volume) solvent mixture, the Rf is in the region of 0.14 (orange-coloured visualization with Ehrlich's reagent).

59451 RP is characterized by the following physico-chemical properties:
  appearance: white to pale yellow amorphous powder
  solubility: soluble in methanol, ethanol, ethyl acetate, acetone, acetonitrile, dimethylformamide, dimethyl sulphoxide, insoluble in water (0.1 to 0.3% regardless of the pH), ethyl ether and hexane
  percentage composition: 59451 RP corresponds to the empirical formula $C_{46}H_{47}N_7O_{12}$. The percentage composition is:

|       | calculated | found (without modification) |
|-------|------------|------------------------------|
| C %   | 62.09      | 58.64                        |
| H %   | 5.32       | 5.42                         |
| N %   | 11.02      | 10.47                        |
| O %   | 21.57      | 25.10                        |
| H$_2$O % | —       | 5.37                         | melting point: 275°–280° C. (decomposition)
optical rotation: $[\alpha]_D^{20} = +24.3° \pm 1°$ (c=0.5, methanol).

The structure of 59451 RP was determined from its ultraviolet, infrared and mass spectra and proton and $^{13}C$ nuclear magnetic resonance spectra.

Ultraviolet spectrum (determination using a methanolic solution containing 38 μg/ml, on a thickness of 1 cm):

$\lambda \text{max} = 268$ nm ($E_{1\,cm}^{1\%} = 223$, $\epsilon = 19864$)

Figure 3:
FIGS. 3 and 4 of the accompanying drawings show respectively the ultra-violet and infra-red spectra of 59451 RP.

The ultraviolet spectrum of 59451 RP is shown in FIG. 3.

Infrared spectrum: (determination using tablets of a mixture with KBr)

Figure 4:
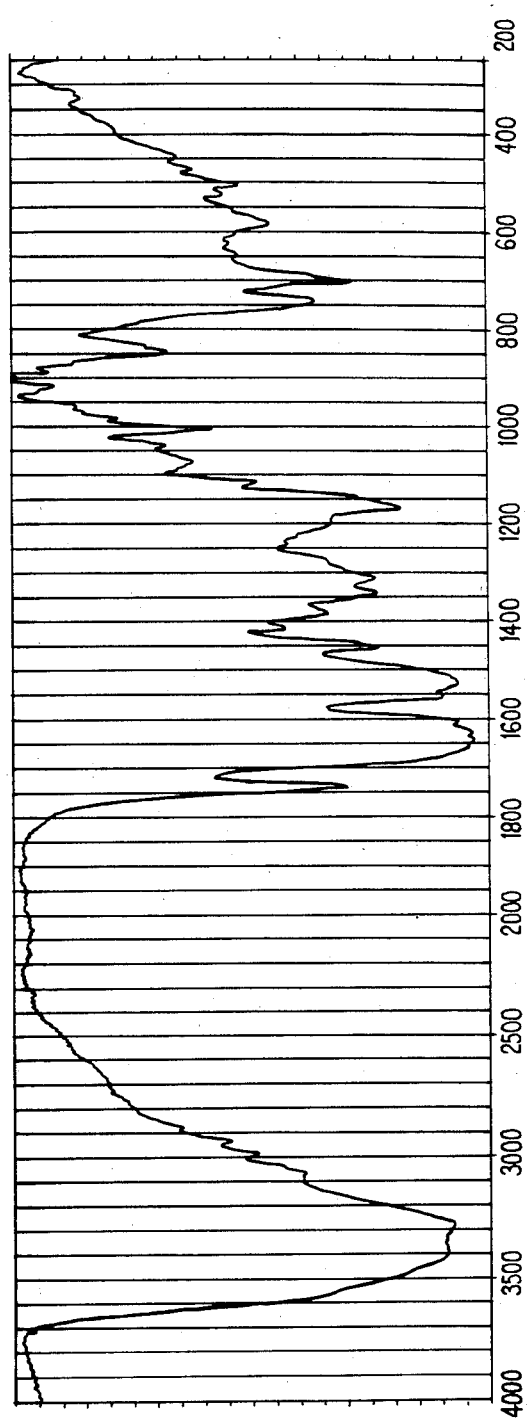

The infrared spectrum is shown in FIG. 4, in which the wave numbers in cm$^{-1}$ are plotted as abscissae and the optical densities as ordinates.

Table III shows the main infrared absorption bands of 59451 RP expressed as wave numbers (cm$^{-1}$).

TABLE III

| 3360 sh | 1455 m | 920 w |
|---|---|---|
| 3480 sh (including H$_2$O) | 1445 sh | 900 vw |
| 3400 vS | 1415 m | 885 vw |
| 3280 vS | 1380 m | 870 sh |
| 3060 sh | 1340 m | 850 m |
| 3040 sh | 1310 m | 830 sh |
| 2980 w | 1295 sh | 785 sh |
| 2940 w | 1275 sh | 750 sh |
| 2880 sh | 1245 vw | 740 S |
| 2680 sh | 1230 sh | 700 S |
| 2520 sh | 1190 sh | 690 sh |
| 2160 sh | 1170 S | 645 vw |
| 2060 sh | 1145 sh | 620 vw |
| 1950 sh | 1110 m | 605 vw |
| 1880 sh | 1090 sh | 585 m |
| 1740 sh | 1070 w | 550 sh |
| 1675 sh | 1060 sh | 520 vw |
| 1655 sh | 1040 w | 505 m |
| 1640 vS | 1030 sh | 470 vw |
| 1625 vS | 1000 m | 445 vw |
| 1605 S | 990 vw | 400 sh |
| 1555 S | 970 sh | 330 sh |
| 1530 S | 960 vw | |
| 1500 sh | 930 sh | | vS = very strong
vw = very weak
S = strong
w = weak
m = moderate
sh = shoulder

Mass spectrum

In FAB ionization (fast atom bombardment with an 8 keV beam of xenon atoms) with a glycerol/thioglycerol mixture as matrix, the base peak is the pseudomolecular ion MH$^+$ = 890.

Ions are observed at masses m/z=781 and m/z=650.
The ion observed at mass m/z=650 corresponds to the fragment:

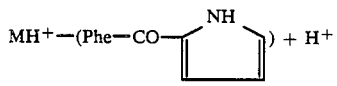

In desorption/chemical ionization (DCI) with $NH_3$ as the reactant gas, fragments of mass m/z=241 and m/z=341 are obtained, the fragments corresponding to the following structures:

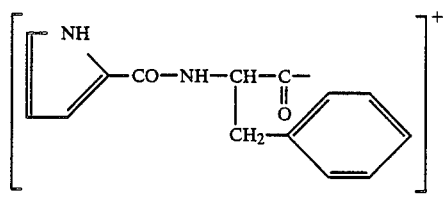

and

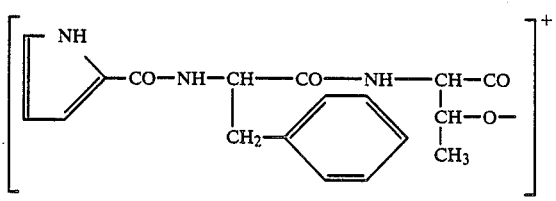

Proton and $^{13}C$ nuclear magnetic resonance spectra:

The spectra were recorded in DMSO-$d_6$, working at 250 MHz for protons and at 100.6 MHz for carbon.

The assignments are given in ppm relative to the central line of DMSO (2.5 ppm for protons; 39.5 ppm for carbon).

The analysis of the proton nuclear magnetic resonance spectrum is given in Table IV.

TABLE IV

|     | Hα        | Hβ              | Hγ              | NH               | Aromatic              | OH        |
|-----|-----------|-----------------|-----------------|------------------|-----------------------|-----------|
|     | —         | 4.5 (m)         | 5 (m)           | 8.75 (d)         | —                     | —         |
|     |           |                 | 1.10 (d) J = 6 Hz | J = 8 Hz       |                       |           |
| A   | 3.95 (m)  | 1.35 (d) J = 7 Hz | —             | 8.25 (d) J = 5 Hz | —                  | —         |
| $F_1$ | 4.8 (m) | 3 (m)           | —               | 8.15 (d) J = 9 Hz | 7 to 7.40           | —         |
| $F_2$ | 4.5 (m) | 3 (m)           | —               | 6.75 (d) J = 8 Hz | 7 to 7.40           | —         |
| $FS_1$ | 5.45 (d) | —            | —               | 7.85 (d) J = 9 Hz | 6.2 to 6.3          | 9.35 (bs) |
| $FG_2$ | 5.25 (d) J = 8 Hz | —    | —               | 8.35 (d) J = 8 Hz | 6.2 to 6.3          | 8.25 (bs) |
| P   | —         | —               | —               | 11.45 (bs)       | 6.95; 6.85 and 6.10 (3 × m) | —    |

The coupling constant J is expressed in Hz

| d = doublet | s = singlet |
|---|---|
| bs = broad singlet | m = multiplet |
| T = threonine | A = alanine |
| F = phenylalanine | FG = phenylglycine |
| P = pyrrole | |

The $^{13}C$ nuclear magnetic resonance spectrum of 59451 RP is identical to that of 55185 RP to within ±0.2 ppm, with the exception of the pyrrole portion:

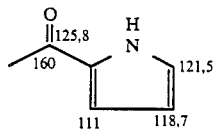

In ascending thin layer chromatography on silica gel, using a 1,2-dichloroethane/methanol (80:20 by volume) solvent mixture, the Rf is in the region of 0.5. On Merck silanized silica plates, using an acetonitrile/water containing 3% of NaCl (40:60 by volume) solvent mixture, the Rf is in the region of 0.21 (brick-red coloured visualization with Ehrlich's reagent).

55185 RP and 59451 RP may be characterized by coloured reactions with different reagents. They give positive reactions with iodine, Gibb's reagent, sulphuric vanillin, ferric chloride, Greig-Leaback reagent (chlorine/tolidine) and Ehrlich's reagent. They give negative reactions with ninhydrin and Dragendorff's reagent.

The microorganism which produces 55185 RP and 59451 RP is a strain of Actinomycetales which was isolated from a soil sample taken at Escandon in Spain and to which the number S-16328 was assigned. A sample of this microorganism was deposited under the Budapest Treaty at the Centraalbureau voor Schimmelcultures at Baarn (Netherlands) on Mar. 24, 1986, where it has been given the deposit number CBS 162.86.

This microorganism has features which differentiate it from species already described, and must therefore be considered to be new. It has been assigned the designation Streptomyces sp. S-16328.

The microorganism was isolated by following the general method which consists in suspending a small amount of soil in sterile distilled water, diluting the suspension to different concentrations and plating a small volume of each dilution on the surface of a Petri dish containing an agar nutrient medium. After a few days' incubation at 26° C., which enables the microorganisms to grow, the colonies which it is desired to isolate, so that they may be studied further, are removed and subcultured on nutrient agars in order to obtain more prolific cultures.

The actinomycete S-16328 belongs to the family of Streptomycetaceae genus Streptomyces, since its cell wall contains 2,6-diamino-L-pimelic acid.

Streptomyces S-16328 forms cylindrical spiny spores measuring 0.4 to 0.6 μm/1 to 1.2 μm. Its straight or flexuous sporiferous chains (aerial hyphae) are long and generally contain tens of spores. The sporophores are simple. On the basis of its mode of sporulation, this strain is classified in the Rectus-Flexibilis Section of Pridham's classification.

Streptomyces S-16328 possesses a pink-beige coloured sporulated aerial mycelium. It grows well at 28° C. The colouring of its vegetative mycelium generally varies, according to the culture medium, from yellowish white to beige-brown.

The new Streptomyces does not give a soluble pigment on the media on which it has been observed. In these cultures, performed at 28° C., it possesses the following biochemical features:

| | |
|---|---|
| melanin production | negative |
| $H_2S$ production | negative |
| tyrosinase | positive |
| hydrolysis of casein | positive |
| hydrolysis of gelatin | positive |
| production of nitrites from nitrates | negative |
| hydrolysis of starch | positive |
| culturing on milk | peptonization without coagulation, with alkalinization of the pH, which changes from 6.4 to 7.5 in the course of 28 days |

Culturing features of the Streptomyces are collated in Table V. These apply to cultures which have reached a good stage of growth, that is to say from 2 to 3 weeks at 28° C. These features were observed on nutrient agars and broths (liquid culture media) which are commonly used for determining the morphological features of Streptomyces strains. The culturing on agar media was performed in Petri dishes, except for the media $ISP_6$, $ISP_7$ and Waksman's melanin, when it was carried out on agar slopes. The references or compositions of the culture media are as follows:

Ref. 1: "Methods for characterization of Streptomyces species", International Journal of Systematic Bacteriology—E. B. Shirling and D. Gottlieb, vol. 16, No. 3, 1966 p. 313–340

Ref. 2: "Melamin formation medium" S. A. Waksman, The Actinomycetes, vol. 2, No. 42, p. 333, The Williams and Wilkins Company, Baltimore, 1961

Ref. 3: "Manual of Methods for Pure Culture Study of Bacteria", Society of American Bacteriologists, Geneva, N.Y. $II_{50}$-18

Ref. 4: "The Taxonomy of soil Bacteria"—R. E. Gordon, Ecology of Soil Bacteria, Liverpool University Press 1967, T. R. G. Gray, B. Parkinson Ed.

Ref. 5: Plain Gelatin, prepared according to the directions in the "Manual of Methods for Pure Culture Study of Bacteria", Society of American Bacteriologists, Geneva, N.Y. $II_{50}$-18

Ref. 6: Commercial powdered skimmed milk reconstituted according to the manufacturer's directions.

TABLE V

| Culture medium | Extent of growth | Vegetative mycelium or underside of the culture | Aerial apparatus (comprising the whole aerial mycelium and sporulation system) | Soluble pigment | Observations and biochemical properties |
|---|---|---|---|---|---|
| $ISP_1$ (ref. 1) | good | yellowish white profuse-puckered | 0 | 0 | — |
| $ISP_2$ (ref. 1) | good | beige-brown profuse-puckered | whitish in the trace state spores = 0 | 0 | — |
| $ISP_3$ (ref. 1) | moderate | greyish white | 0 | 0 | — |
| $ISP_4$ (ref. 1) | very good | yellowish beige puckered | pink-beige many spores | 0 | utilization of starch |
| $ISP_5$ (ref. 1) | slight | greyish beige puckered | 0 | 0 | — |
| $ISP_6$ (ref. 1) | fairly good | whitish puckered profuse | 0 | 0 | $H_2S$ production negative |
| $ISP_7$ (ref. 1) | fairly good | yellowish white puckered | 0 | faint pink-brown soluble pigment | melanin production negative |
| Waksman's melanin agar (ref. 2) | poor | whitish slight | 0 | 0 | melanin production negative |
| Difco nitrate nutrient broth (ref. 3) | moderate | whitish flocculent culture | 0 | 0 | nitriate formation negative |
| casein agar (ref. 4) | good | yellowish white to yellowish brown profuse and puckered | 0 | 0 | very fast hydrolysis of casein |
| tyrosine agar | good | yellowish white puckered | whitish, growth very slight | 0 | very fast degradation of tyrosine |
| culture on | moderate | whitish | 0 | 0 | liquefaction of the |

TABLE V-continued

| Culture medium | Extent of growth | Vegetative mycelium or underside of the culture | Aerial apparatus (comprising the whole aerial mycelium and sporulation system) | Soluble pigment | Observations and biochemical properties |
|---|---|---|---|---|---|
| pur 12% strength gelatin (ref. 5) | | | | | gelatin positive and complete after 7 days of culture |
| Skimmed milk (ref. 6) | 28° C. good | well developed yellowish ring | white, not very profuse | | peptonization without coagulation, pH changing from 6.4 to 7.5 in 1 month (control 6.25, 6.20) |
| | 37° C. good | fairly well developed brownish ring | 0 | | peptonization without coagulation, pH changing from 6.43 to 6.80 in 1 month (control pH 6.16, 6.11) |

Physiological tests on Streptomyces sp. S-16328 were run using the ISP carbohydrate utilization media and the test series of Mishra, S. J., Gordon, R. E. and Barnett, D. A. J. of Clinical Microbiology 11: 728–736, 1980. The results of these two series are summarized in Tables VI and VII respectively. These data show that strain S16328 is very similar to *Streptomyces durhamensis*, Gordon, M. and Lapa, E. Appl. Microbiol. 14: 754–760, 1966, as represented by strain ISP 5539 and differs in 6 of 55 tests in the Gordon series. S16328 and ISP 5539 differ very litte in aerial coloration, both being somewhat grayish-brown, and both having spiny spores.

TABLE VI

Carbohydrate Utilization by S16328 and ISP 5539 (ISP Basal Medium)

| Carbohydrate | S16328 | ISP 5539 |
|---|---|---|
| Arabinose | + | + |
| Fructose | + | + |
| Glucose | + | + |
| Inositol | + | + |
| Mannitol | + | + |
| Raffinose | + | + |
| Rhamnose | − | − |
| Sucrose | + | + |
| Xylose | + | + |

TABLE VII

Test Reactions of Streptomyces S16328 and *Streptomyces durhamensis* ISP 5139 (Gordon Tests)

| | S16328 | ISP 5539 |
|---|---|---|
| Degradation/Transformation of | | |
| Casein | + | + |
| Xanthine | + | + |
| Hypoxanthine | + | + |
| Tyrosine | + | + |
| Adenine | + | + |
| Melanoid Pigment | − | + |
| Production of | | |
| Amylase | + | + |
| Gelatinase | + | + |
| Phosphatase | + | + |
| Nitrate Reductase | − | − |
| Urease | + | + |
| Esculinase | + | + |
| Growth on/in | | |
| 5% NaCl | + | − |
| Salicylate | ± | − |
| Lysozyme Broth | + | + |
| Utilization | | |
| Acetate | + | + |
| Benzoate | − | − |
| Citrate | + | + |
| Lactate | + | + |
| Malate | + | + |
| Mucate | − | − |
| Oxalate | + | − |
| Propionate | + | + |
| Pyruvate | + | + |
| Succinate | + | + |
| Tartrate | − | − |
| Growth at | | |
| 10° C. | + | − |
| 45° C. | − | − |
| 53° C. | − | − |
| Acid from | | |
| Adonitol | + | + |
| Arabinose | + | + |
| Cellobiose | + | + |
| Dextrin | + | + |
| Dulcitol | − | − |
| Erythritol | − | − |
| Fructose | + | + |
| Galactose | + | + |
| Glucose | + | + |
| Glycerol | + | + |
| Inositol | + | + |
| Lactose | + | + |
| Maltose | + | + |
| Mannitol | + | + |
| Mannose | + | + |
| Melibiose | + | + |
| α-Me—D-Glucoside | + | + |
| Raffinose | + | + |
| Rhamnose | − | − |
| Salicin | + | + |
| Sorbitol | − | − |
| Sucrose | + | + |
| Trehalose | + | + |
| Xylose | + | + |
| β-Me—D-Xyloside | + | − |

The process for preparing 55185 RP and 59451 RP consists essentially in culturing Streptomyces sp. S-16328, or a productive mutant thereof, on a nutrient medium under suitable conditions, and in separating and purifying the product formed during the culture.

The culturing of Streptomyces sp. S-16328 can be performed by any surface or submerged aerobic culture method, but the latter type of method is to be preferred for reasons of convenience. For this purpose, the various types of apparatus which are commonly used in the fermentation industry can be employed.

In particular, the following sequence may be adopted for performing the operations:

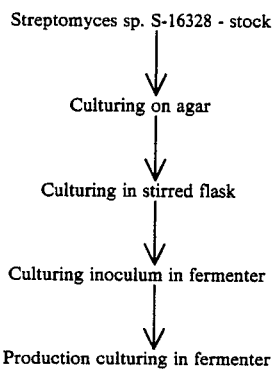

The fermentation medium must contain principally a source of assimilable carbon and a source of assimilable nitrogen, inorganic elements, in particular chlorides, and, where appropriate, growth factors, it being possible for all these components to be supplied in the form of well-defined products or by complex mixtures such as are encountered in biological products of various origins.

As sources of assimilable carbon, it is possible to use carbohydrates such as glucose, sucrose, maltose, dextrins, starch or other carbohydrate substances such as sugar alcohols (glycerol) or such as certain organic acids, eg. lactic and citric acids. Certain animal or vegetable oils, such as lard oil or soya bean oil can advantageously replace these different carbohydrate sources, or be combined with them.

The sources of assimilable nitrogen which are suitable are extremely varied. They may be simple chemical substances such as inorganic or organic ammonium salts, urea or certain amino acids. They may also be supplied by complex substances mainly containing nitrogen in protein form: e.g. casein, lactalbumin, gluten and the hydrolysates of these substances, soya flour, groundnut flour, fish meal, meat and yeast extracts, distillery solubles and corn steep.

Among the added inorganic components, some may have a buffering or neutralizing effect, such as alkali metal or alkaline earth metal phosphates or calcium and magnesium carbonates. Others provide the ion balance required for the growth of Streptomyces sp. S-16328 and for the formation of 55185 RP and 59451 RP, such as alkali metal or alkaline earth metal chlorides and sulphates. Finally, some act more especially as activators of the metabolic reactions of Streptomyces sp. S-16328, this being the case with zinc, cobalt, iron, copper and manganese salts.

The growth factors are products of a vitamin nature, such as riboflavin, folic acid and pantothenic acid.

The pH of the fermentation medium at the start of culturing should be between 5.8 and 7.8, and preferably between 6.2 and 7.4. The optimum temperature for the fermentation is between 25° and 30° C., but satisfactory production is obtained with temperatures of between 23° and 33° C. The aeration of the fermentation medium may vary within wide limits. It has, however, been found that aerations of 0.3 to 3 liters of air per liter of broth per minute are especially suitable. The maximum yield of 55185 RP is obtained after 2 to 8 days of culture, this time depending chiefly on the medium used.

From the foregoing, it will be understood that the general conditions of culturing Streptomyces sp. S-16328 for the production of 55185 RP and 59451 RP can vary over a wide range and can be adapted to each particular requirement.

55185 RP and 59451 RP may be isolated from fermented medium in the following manner:

The medium is filtered at a pH which is generally between 6 and 8, preferably about 7, in the presence of a filter aid.

The 55185 RP and 59451 RP retained in the filter cake are extracted therefrom with a suitable organic solvent, e.g. a ketone such as acetone or an alcohol such as methanol. The crude product may be isolated from the organic solutions by crystallization after concentration of these solutions under reduced pressure, addition, where appropriate, of a poor solvent or a non-solvent, and being left for a period in the cold chamber.

55185 RP and 59451 RP may be separated and purified by customary methods, such as recrystallization, chromatography on various adsorbent supports or countercurrent distribution.

59451 RP may also be obtained by dechlorination of 55185 RP according to the customary methods which enable a chlorine atom to be replaced by a hydrogen atom without affecting the remainder of the molecule.

It is especially advantageous to treat 55185 RP in methanolic solution with gaseous hydrogen in the presence of a catalyst at a temperature in the region of 20° C. As catalyst, palladized charcoal is generally used, in the presence of an acceptor for acid such as magnesium oxide.

The examples which follow illustrate the invention.

EXAMPLE 1 (fermentation)

A 170-liter fermenter is charged with:

| | |
|---|---|
| peptone | 1200 g |
| yeast extract | 600 g |
| Cerelose (dextrose) | 1200 g |
| sodium chloride | 600 g |
| tap water, q.s. | 120 liters |

The pH is adjusted to 7.0 by adding 10N sodium hydroxide solution (30 cc).

The medium is sterilized by bubbling steam at 122° C. through it for 40 minutes. After cooling, the pH of the medium is 6.6.

The medium is seeded with a portion (200 cc) of a 72-hour stirred Erlenmeyer culture of Streptomyces sp. S-16328.

The culture is grown at 28° C. for 36 hours, stirring at 250 revolutions/minute and aerating with sterile air at a flow rate of 5 m³/hour. It is then suitable for seeding the production culture.

The production culturing is performed in an 800-liter fermenter in which the following substances are charged:

| | |
|---|---|
| sterilized distillery solubles | 10 kg |
| sterilized Cerelose | 4 kg |
| soya bean oil | 2 liters |
| calcium carbonate | 2 kg |
| sterilized ammonium sulphate | 0.8 kg |

| -continued | |
|---|---|
| tap water, q.s. | 400 liters |

The pH is adjusted to 7.0 by adding 10N sodium hydroxide solution (440 cc).

The medium is sterilized by bubbling steam at 122° C. through it for 40 minutes after it has been heated for 15 minutes at 100° C.

The pH of the medium is then 6.75.

It is then seeded with the inoculum culture (40 liters) prepared in the 170-liter fermenter, described above.

The culture is grown at 26° C. for 83 hours, stirring at 250 revolutions/minute and aerating with sterile air at a flow rate of 20 m$^3$/hour.

At the end of the operation, the pH of the culture is 8.05 and the volume of the fermented medium is 410 liters.

EXAMPLE 2 (Extraction-Purification)

The fermented medium (400 liters) is filtered in the presence of a filter aid (Clarcel; 20 kg) on a filter press. The filter cake containing the mycelium is broken up with vigorous stirring in acetone (200 liters) containing 20% of water. The suspension is filtered on a filter press in the presence of filter aid. The filtrate obtained is concentrated under reduced pressure to remove the acetone. The residual aqueous solution is extracted at a pH in the region of 7 with ethyl acetate (2×50 liters). The organic phase is separated by decantation and then concentrated to dryness under reduced pressure (2–3 torrs; 0.27–0.4 kPa). An oily residue (183 g) is thereby obtained.

The oily residue is dissolved in methanol (1.5 liter) and then deposited by evaporation under reduced pressure (2–3 torrs; 0.27–0.4 kPa) on "Duolite S 861" resin (500 cc). The resin is charged at the top of a column 7.5 cm in diameter containing "Duolite S 861" resin (3 liters) equilibrated in a methanol/water (50:50 by volume) mixture. Elution is performed at a flow rate of 640 cc/hour, taking fractions every 30 minutes, and eluting successively with:

methanol/water (50:50 by volume): fractions 1 to 34
methanol/water (70:30 by volume): fractions 35 to 71
methanol/water (80:20 by volume): fractions 72 to 100

Each fraction is monitored by thin layer chromatography on silica gel, eluting with a 1,2-dichloroethane/methanol (80:20 by volume) system and visualizing, for an Rf in the region of 0.5, with Gibb's reagent, which gives a characteristic blue colour with compounds containing a phenol group.

Most of the 55185 RP is in fractions 87 to 97, which are combined and then deposited by evaporation under reduced pressure (2–3 torrs; 0.27–0.4 kPa) on "GRACE 60 Å" silica gel (40–63 microns) (400 cc).

The dry powder obtained is deposited on a column, 7.5 cm in diameter and 110 cm high, of silica equilibrated in a 1,2-dichloroethane/methanol (80:20 by volume) mixture. An isocratic elution is performed at a flow rate of 600 cc/hour. The 55185 RP is eluted in fractions 6 to 15. The last three fractions which contain a yellow pigment are removed. After evaporation of the combined fractions 6 to 12 under reduced pressure (2–3 torrs; 0.27–0.4 kPa), a beige gummy solid (6.8 g) is obtained.

The product thereby obtained is taken up with methanol (50 cc). The solution is filtered, then concentrated to a volume of 5 cc and finally deposited on a column, 5 cm in diameter and 138 cm high, of Sephadex LH-20 set up in methanol. Elution is performed with pure methanol at a flow rate of 300 cc/hour, collecting fractions every 20 minutes. The fractions are monitored by thin layer chromatography. Fractions 10 to 13 which contain the 55185 RP are combined and concentrated to a volume of 100 cc. Cyclohexane (150 cc) is then added. After stirring followed by decantation, the methanol phase is concentrated to dryness under reduced pressure (2–3 torrs; 0.27–0.4 kPa). 55185 RP (2.32 g) containing 6% of 59451 RP is thereby obtained.

EXAMPLE 3

The fermented medium (400 liters) is filtered in the presence of a filter air (Clarcel; 20 kg) on a filter press. The filter cake containing the mycelium is broken up with vigorous stirring in acetone (200 liters) containing 20% of water. The suspension is filtered on a filter press in the presence of a filter aid. The filtrate obtained is concentrated under reduced pressure to remove the acetone. The residual aqueous solution is extracted at a pH in the region of 7 with ethyl acetate (2×50 liters). The organic phase is separated by decantation and then concentrated to dryness under reduced pressure (2–3 torrs; 0.27–0.4 kPa). An oily residue is thereby obtained.

The oily residue thereby obtained is taken up with methanol (5 liters). Cyclohexane (15 liters) is added with stirring. After decantation, the methanol phase is evaporated under reduced pressure and the residue is dispersed in ethyl ether (1 liter). A fine powder (32.5 g) is formed, and this is separated by filtration.

The powder (26 g) obtained is taken up with methanol (500 cc) and the solution obtained is adsorbed on silica gel (particle size: 35–70 microns; porosity 60 Å) (185 g). The dry powder is charged in a 400-cc column, which is filled with silica gel. Elution is performed with pure ethyl acetate (1 liter). After being concentrated to dryness, the solution obtained yields a yellow powder (11.7 g).

10 g of the powder obtained above is taken up in methanol (150 cc) and the solution obtained is adsorbed on grafted silica (GRACE C 18: particle size 20 microns; porosity 100 Å) (100 cc). The dry powder obtained is charged in a "pre-column" (diameter 7.5 cm; height 10 cm) which is then filled up with the grafted silica. After the "pre-column" is closed, the air contained in it is driven out with a stream of distilled water, and the distilled water is displaced with 40% acetonitrile (400 cc).

The "pre-column" is then connected to a column (diameter 7.5 cm; height 50 cm) containing the same chromatographic support equilibrated in 40% acetonitrile. An isocratic elution is performed at a flow rate of 150 cc/minute, collecting 500-cc fractions. The fractions are monitored by thin layer chromatography on MERCK silanized silica plates, which are eluted with an acetonitrile/3% strength aqueous sodium chloride solution (40:60 by volume) mixture.

The eluted products are distinguished by their colour with Ehrlich's reagent and their Rf.

Fractions 12 to 15 contain a product (0.46 g) whose Rf=0.21, which gives a brick-red colour with Erlich's reagent and which corresponds to 59451 RP.

Fractions 18 to 51 contain a product (5.96 g) whose Rf=0.14, which gives an orange colour with Erlich's reagent and which corresponds to 55185 RP.

1.13 g of the product whose Rf=0.21 is taken up in a methanol/water (65:35 by volume) mixture (15 cc).

The clear solution is injected onto a column (diameter 5 cm; length 50 cm) of MCI gel CHP 20P equilibrated in the same solvent mixture. An isocratic elution is performed at a flow rate of 17 cc/minute, collecting 50 100-cc fractions, and elution is then continued with a methanol/water (72:28 by volume) mixture under the same conditions. A further 60 fractions are thereby collected.

Fractions 78 to 110 yield pure 59451 RP (0.59 g).

10.5 g of the product whose Rf=0.14 are taken up in 65% methanol (350 cc). The clear solution is injected onto a column (diameter 5 cm; length 50 cm) of MCI gel CHP 20P equilibrated in 65% methanol. Elution is performed under the same conditions as above, at a flow rate of 17 cc/minute with 65% methanol (4 liters) and then with 85% methanol (4 liters), collecting 100-cc fractions.

Fractions 46 to 56 yield pure 55185 RP (9.78 g).

EXAMPLE 4

Pure 55185 RP (14 g) is added to a suspension of palladinized charcoal (5% palladium) (3.5 g) and magnesium oxide (MgO) (3.5 g) in methanol (120 cc).

Hydrogen is passed through in the form of a stream of individual bubbles, at a temperature in the region of 20° C. and under 760 mm Hg (101.3 kPa) for 15 hours.

Analysis by high performance liquid chromatography shows that the dechlorination of 55185 RP to 59451 RP is quantitative.

The reaction mixture is filtered in the presence of a filter aid (Celite). After evaporation of the filtrate to dryness, a white powder (15.2 g) containing residual methanol is obtained.

11 g of the powder thereby obtained is taken up with methanol (150 cc). The solution is adsorbed on grafted silica (GRACE N.D. C18) of particle size 35–70 microns.

The dry powder obtained is charged in the dry state in a "pre-column" (diameter 7.5 cm; height 10 cm), filling up with a fresh portion of the same grafted silica. After the "pre-column" is closed, the air contained in it is driven out with a stream of distilled water, and the latter driven out with 40% acetonitrile (400 cc).

The "pre-column" is then connected to a column 7.5 cm in diameter and 50 cm high containing the same C18 grafted silica but having a particle size of 20 microns, equilibrated in 40% acetonitrile.

An isocratic elution is performed at a flow rate of 150 cc/minute, collecting 500-cc fractions after the passage of 1.3 liter of eluent.

After evaporation under reduced pressure, fractions 8 to 12 yield 59451 RP (8.9 g), which is purified under the conditions described in Example 3.

55185 RP and 59451 RP show exceptional immunosuppressant properties. More especially, 55185 RP and 59451 RP are immunosuppressants of cellular immunity.

In vitro, at molar concentrations of between $10^{-5}$ and $10^{-8}$, 55185 RP and 59451 RP significantly inhibit:

the cytostatic activity of thioglycolate-induced mouse peritoneal macrophages, especially if the latter have been stimulated by adding interleukin-2 to the lymphocytes during the incubation phase [GYON-GYOSSI M.I.C. et al., Cell. Immunol. 45, 1 (1979)]

the production of interleukin-2 by human lymphocyte stimulated by phytohaemagglutin (PHA) [WATSON J. and MOCHIZUKI D., Immunolog. Rev. 51, 257 (1980)] or by mouse thymocytes stimulated with PHA and interleukin-1 the production of gamma interferon by human lymphocytes or by mouse thymocytes [FARRAR W. L. et. al., J. Immunol. 126, 1120 (1981)].

In vitro, 55185 RP and 59451 RP do not exhibit an inhibitory effect on antibody secretion [using the techniques of P. H. Klesius, Proc. Soc. Exp. Biol. Med. (N.Y.), 135, 155 (1970) and de H. van Dijk and N. Bloksma, J. Immunol. Methods 14, 325 (1977)], and they are virtually devoid of cytotoxicity for leukaemia P388 cells.

When administered to mice at doses of between 25 and 50 mg/kg i.p. one day before the test, 55185 RP and 59451 RP inhibit the measured NK activity towards YAC/1 target cells [HERBERMAN, R. B. et al., Int. J. Cancer 16, 216 (1975)].

When administered orally at a dose of 50 mg/kg for 10 days, 55185 RP and 59451 RP significantly delay allergenic ($C_{57}B1/6$) skin graft rejection in Balb/c mice, or semi-allergenic ($B_6D_2F_1$) skin graft rejection in $C_{57}B1/6$ mice.

Furthermore, 55185 RP and 59451 RP show no effect, or show a stimulatory effect, on the production of plaque-forming cells [using the technique of N. K. Jerne and A. A. Nodin, Science, 140, 405 (1963)]. They have no effect on the growth of leukaemia P388 in mice when they are administered at doses of between 12.5 and 50 mg/kg i.p. for 4 days.

In human therapy, 55185 RP and 59451 RP are especially useful for combating the rejection of organ or tissue transplants, and for the treatment of autoimmune diseases such as rheumatism, insulin-dependent diabetes, multiple sclerosis, myasthaenias, lupus, psoriasis and Crohn's disease.

In human therapy, the appropriate dosage depends on the effect sought and on the period of treatment. It is generally between 0.5 and 100 mg/kg/day orally and between 0.1 and 20 mg/kg/day parenterally for an adult. In general, the doctor will determine the dosage which he considers most suitable according to the age, weight and all other factors specific to the subject to be treated.

The invention includes within its scope pharmaceutical compositions containing 55185 RP and/or 59451 RP in association with a pharmaceutically acceptable diluent or coating. These compositions may be used orally, rectally or parenterally.

As solid compositions for oral administration, tablets, pills, powders or granules may be used. In these compositions, the active ingredient according to the invention is mixed with one or more inert diluents such as sucrose, lactose or starch. These compositions can also include substances other than diluents, for example a lubricant such as magnesium stearate.

Liquid compositions for oral administration may be pharmaceutically acceptable emulsions, solutions, suspensions, syrups and elixirs containing inert diluents such as water or liquid paraffin. These compositions can also include substances other than diluents, for example wetting, sweetening or flavouring agents.

The compositions for parenteral administration can be aqueous or non-aqueous sterile solutions, suspensions or emulsions. As a solvent or vehicle, it is possible to use propylene glycol, polyethylene glycol, vegetable oils, especially olive oil, and injectable organic esters, e.g. ethyl oleate.

These compositions can also contain additives, especially wetting agents, emulsifiers and dispersants. The sterilization can be carried out in several ways, e.g. by means of a bacteriological filter, by incorporating sterilizing agents in the composition, by irradiation or by heating. They may also be prepared in the form of sterile solid compositions which can be dissolved at the time of use in an injectable sterile medium.

The compositions for rectal administration are suppositories which can contain, in addition to the active principle, excipients such as cocoa butter or semi-synthetic triglycerides.

The Examples which follow illustrate compositions according to the invention.

EXAMPLE A

According to the customary technique, tablets are prepared containing a 25-mg dose of 55185 RP and having the following composition:

| | |
|---|---|
| 55185 RP | 0.025 g |
| starch | 0.090 g |
| precipitated silica | 0.030 g |
| magnesium stearate | 0.005 g |

EXAMPLE B

According to the customary technique, a solution for parenteral administration having the following composition is prepared:

| | |
|---|---|
| 55185 RP | 0.5 g |
| injectable solution | 5 cc |

EXAMPLE C

According to the customary technique, tablets are prepared containing a 25-mg dose of 59451 RP and having the following composition:

| | |
|---|---|
| 59451 RP | 0.025 g |
| starch | 0.090 g |
| precipitated silica | 0.030 g |
| magnesium stearate | 0.005 g |

EXAMPLE D

According to the customary technique, a solution for parenteral administration having the following composition is prepared:

| | |
|---|---|
| 59451 RP | 0.5 g |
| injectable solution | 5 cc |

We claim:

1. An immunosuppressant cyclodepsipeptide of the formula:

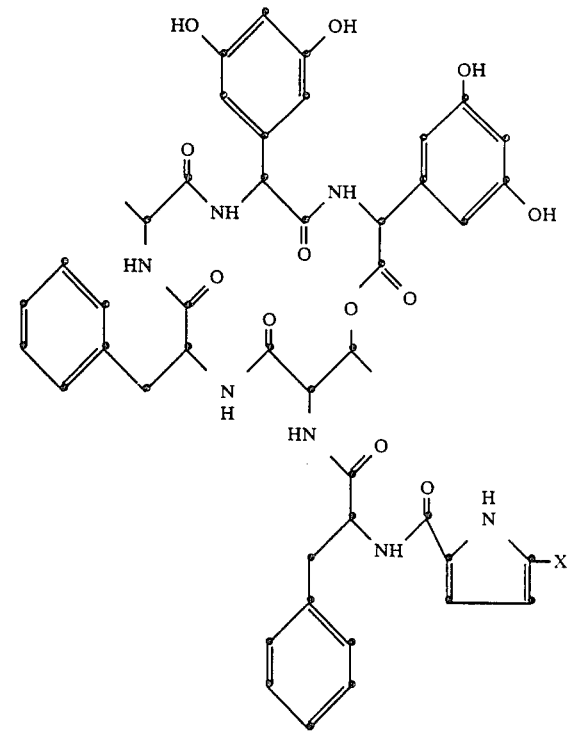

in which X is chlorine (55185 RP) or hydrogen (59451 RP).

2. An immunosuppressant substance designated herein 55185 RP, having the following properties:

it is a white to pale yellow amorphous powder, soluble in methanol, ethanol, ethyl acetate, acetone, acetonitrile, dimethylformamide, and dimethyl sulphoxide, and insoluble in water, ethyl ether and hexane;

its empirical formula is $C_{46}H_{46}ClN_7O_{12}$;

its elementary composition is approximately: $C\% = 58.29$, $H\% = 5.30$, $Cl\% = 3.84$, $N\% = 10.13$, and $O\% = 22.57$;

its melting point is above 300° C.;

its optical rotation, determined in methanol (C=0.5), is $[\alpha]_D^{20} = +20.5° \pm 1.4°$;

its ultraviolet spectrum in methanol shows a shoulder at 230 nm and an absorption maximum at 274 nm ($E_{1\ cm}^{1\%} = 219$; $\epsilon = 20240$);

its infrared spectrum, determined using tablets of a mixture with KBr, shows the following characteristic absorption bands: 3380, 3300, 3090, 3060, 3030, 2980, 2940, 2880, 2700, 2500, 2340, 2160, 1950, 1880, 1740, 1680, 1655, 1625, 1605, 1555, 1520, 1500, 1455, 1440, 1425, 1405, 1380, 1340, 1310, 1285, 1215, 1205, 1160, 1120, 1080, 1060, 1050, 1030, 1010, 1000, 980, 950, 925, 900, 850, 795, 785, 750, 700, 690, 635, 625, 605, 580, 525, 510, 495, 455, 450 and 355 cm$^{-1}$; and in ascending thin layer chromatography on silica gel, using a 1,2-dichloroethane/methanol (80:20 by volume) mixture as solvent, it has an Rf of 0.5.

3. An immunosuppressant substance designated herein 59451 RP, having the following properties:

it is a white to pale yellow amorphous powder, soluble in methanol, ethanol, ethyl acetate, acetone, acetonitrile, and dimethyl sulphoxide, and insoluble in water, ethyl ether and hexane;

its empirical formula is $C_{46}H_{47}N_7O_{12}$;

its elementary composition is approximately: C%=62.09, H%=5.32, O%=21.57, N%=11.02;

its melting point is 275°–280° C. (with decomposition);

its optical rotation, determined in methanol, is $[\alpha]_D^{20} = +24.3° \pm 1°$;

its ultraviolet spectrum in methanol shows an absorption maximum at 268 nm ($\epsilon = 19864$)

its infrared spectrum, determined using tablets of a mixture with KBr, shows the following characteristic absorption bands: 3360, 3480, 3400, 3280, 3060, 3040, 2980, 2940, 2880, 2680, 2520, 2160, 2060, 1950, 1880, 1740, 1675, 1655, 1640, 1625, 1605, 1555, 1530, 1500, 1455, 1445, 1415, 1380, 1340, 1310, 1295, 1275, 1245, 1230, 1190, 1170, 1145, 1110, 1090, 1070, 1060, 1040, 1030, 1000, 990, 970, 960, 930, 920, 900, 885, 870, 850, 830, 785, 750, 740, 700, 690, 645, 620, 605, 585, 550, 520, 505, 470, 445, 400, and 330 cm$^{-1}$.

4. A pharmaceutical composition having immunosuppressant acitivity, which contains an effective amount of one or both of the substances 55815 RP and 59451 RP, according to claim 1, in association with a pharmaceutically acceptable diluent or coating.

* * * * *